United States Patent
Fortin

(10) Patent No.: US 10,694,958 B2
(45) Date of Patent: Jun. 30, 2020

(54) WEARABLE HEMODYNAMIC SENSOR

(71) Applicant: CNSYSTEMS MEDIZINTECHNIK AG, Graz (AT)

(72) Inventor: Jurgen Fortin, Graz (AT)

(73) Assignee: CNSYSTEMS MEDIZINTECHNIK AG, Graz (AT)

(*) Notice: Subject to any disclaimer, the term of this patent is extended or adjusted under 35 U.S.C. 154(b) by 380 days.

(21) Appl. No.: 15/535,106

(22) PCT Filed: Jan. 7, 2016

(86) PCT No.: PCT/IB2016/000075
§ 371 (c)(1),
(2) Date: Jun. 12, 2017

(87) PCT Pub. No.: WO2016/110781
PCT Pub. Date: Jul. 14, 2016

(65) Prior Publication Data
US 2017/0367597 A1    Dec. 28, 2017

Related U.S. Application Data

(60) Provisional application No. 62/101,186, filed on Jan. 8, 2015.

(51) Int. Cl.
*A61B 5/02* (2006.01)
*A61B 5/0225* (2006.01)
(Continued)

(52) U.S. Cl.
CPC .......... *A61B 5/02255* (2013.01); *A61B 5/021* (2013.01); *A61B 5/02108* (2013.01);
(Continued)

(58) Field of Classification Search
CPC . A61B 5/02255; A61B 5/021; A61B 5/14551; A61B 5/7278; A61B 5/6843;
(Continued)

(56) References Cited

U.S. PATENT DOCUMENTS

2003/0036685 A1* 2/2003 Goodman ............ A61B 5/0002
600/300
2007/0055163 A1* 3/2007 Asada ................ A61B 5/02225
600/485
(Continued)

FOREIGN PATENT DOCUMENTS

EP            2502555 A1    9/2012
WO    2013/178475 A1    12/2013

OTHER PUBLICATIONS

International Search Report and Written Opinion for PCT App. No. PCT/IB2016/000075, dated Apr. 29, 2016.

*Primary Examiner* — Christian Jang
(74) *Attorney, Agent, or Firm* — McDonnell Boehnen Hulbert & Berghoff LLP

(57) ABSTRACT

A wearable device and the accompanying method for the determination of continuous pulsatile BP are described. The absolute values can be obtained in the initial phase and how a transfer function can transform the BP-signal obtain at the finger or wrist to correct BP-values corresponding to the brachial artery and at heart level. The wearable device contains an orthostatic level-correcting element, which can measure the vertical distance between heart level and finger/wrist level, where the actual measurement takes places. The wearable device may be in the form of a ring, a watch, or a bracelet. Further, the wearable device has elements for wirelessly transmitting signals to host devices such as a smart phone, tablet or other computers.

6 Claims, 7 Drawing Sheets

(51) Int. Cl.
  *A61B 5/021* (2006.01)
  *A61B 5/1455* (2006.01)
  *A61B 5/00* (2006.01)
  *A61B 5/022* (2006.01)
  *A61B 5/024* (2006.01)
  *A61B 5/029* (2006.01)
  *A61B 5/11* (2006.01)

(52) U.S. Cl.
  CPC ...... *A61B 5/02225* (2013.01); *A61B 5/02422* (2013.01); *A61B 5/02438* (2013.01); *A61B 5/14551* (2013.01); *A61B 5/681* (2013.01); *A61B 5/6826* (2013.01); *A61B 5/6843* (2013.01); *A61B 5/721* (2013.01); *A61B 5/7278* (2013.01); *A61B 5/029* (2013.01); *A61B 5/02233* (2013.01); *A61B 5/02241* (2013.01); *A61B 5/1117* (2013.01); *A61B 2560/0261* (2013.01)

(58) Field of Classification Search
  CPC ... A61B 5/6826; A61B 5/681; A61B 5/02438; A61B 5/02422; A61B 5/02225; A61B 5/02108; A61B 5/721; A61B 2560/0261; A61B 5/1117; A61B 5/029; A61B 5/02241; A61B 5/02233
  See application file for complete search history.

(56) References Cited

U.S. PATENT DOCUMENTS

2009/0024011 A1\* 1/2009 Huiku ................ A61B 5/14551
                                                    600/323
2011/0054330 A1    3/2011 Pfeiffer et al.
2011/0105917 A1    5/2011 Fortin et al.

\* cited by examiner

WEARABLE HEMODYNAMIC SENSOR

CROSS REFERENCE TO RELATED APPLICATIONS

The present application is a U.S. National Phase Application pursuant to 35 U.S.C. § 371 of International Application No. PCT/IB2016/000075 filed Jan. 7, 2016, which claims priority to U.S. provisional patent application No. 62/101,186 filed Jan. 8, 2015. The entire disclosure contents of these applications are herewith incorporated by reference into the present application.

FIELD OF THE INVENTION

The application relates generally to a sensor system of measuring blood pressure and further derived hemodynamic parameters, as well as to a method of how continuous hemodynamic readings can be measured with the sensor system. The sensor system is further configured to be wearable.

BACKGROUND

A common modality in medicine is Photoplethysmograpy (PPG), where light from one or more LED's with possibly different wavelengths is transmitted though or reflected from a part of a body and detected by light receivers, such as photo diodes. The photo current is amplified and typically converted into digital signals, whereas the resulting light signal corresponds primarily to blood flow. This PPG-signal is a surrogate of blood pressure, but a translation into blood pressure values with a clinical acceptable accuracy is difficult. The signal is interfered with by noise, especially coming from changes of blood volume caused by vasomotor activity of the arteries. Thus, PPG-based wearable devices usually only measure heart rate, pulse oximetry, or are the second (mostly distal) point of measurement for propagation time methods.

Current wearable BP devices use a method where different sensors measure the propagation time of blood pulses from a proximal body part to a distal body part. This propagation time, which is also called "Pulse Transit Time" (PTT), "Pulse Arrival Time, (PAT)" or other commercially used names, is inversely related to blood pressure. Those PTT-methods and devices do not produce a true pulsatile continuous BP signal, as such devices can only measure one PTT episode per beat. Thus, the BP-signal from those devices cannot be used for further determination of hemodynamic parameters using biomedical algorithms like Pulse Contour Analysis and other pulse related methods. The BP signal measured from those devices needs further calibration with an intermittent upper-arm sphygmomanometer, also called non-invasive BP device (NBP), in a relatively short calibration interval. The calibration interval is dramatically shortened by vasomotoric influences, e.g. thermoregulation, stress or drugs.

Contrary to PTT-methods, WO 2013178475 describes an apparatus and method for the continuous, non-invasive determination of blood pressure (BP) by means of a photoplethysmographic (PPG) system, where the contact pressure of the PPG-system is modified according to the mean arterial pressure (mBP) in the finger. With this method, the true pulsatile BP in the finger or wrist can be obtained by adding the pulsatile PPG-signal PPG(t) multiplied with a calibration factor to the measured contact pressure CP(t) that equals to the mBP.

This method of continuous hemodynamic monitoring according to WO 2013178475 has several limits and cannot be used as a wearable sensor with clinical acceptable accuracy. For example, the system from WO 2013178475 does not allow for the measurement of absolute BP-values and needs persistent NBP calibration. For a wearable device, the permanent use of a NBP on the upper arm is not appropriate.

The system from WO 2013178475 is further influenced by orthostatic pressure difference between heart level and the actual finger level. For a correct use of WO2013178475, the finger or wrist has to be constantly kept on heart level, which is not appropriate for a wearable system.

SUMMARY

In one embodiment, a method for the continuous non-invasive measurement of hemodynamic parameters within a wearable device is disclosed. The method includes measuring a photoplethysmographic signal PPG(t) disposed on a body part containing an artery using a photoplethysmographic system having at least one light source, and at least one light detector generating the photoplethysmographic signal. The contact pressure of the photoplethysmographic system can be varied by an actuator, and the movement of the actuator and the contact pressure is controlled by a control system using at least a part of the photoplethysmographic signal. The true pulsatile BP-signal and further calculated hemodynamic parameters are derived from the contact pressure and the photoplethysmographic signal and from a transfer function and further hemodynamic parameters can be calculated using biomedical algorithms.

In another embodiment, a wearable device for measuring hemodynamic parameters is disclosed. The wearable device includes a photoplethysmographic system having one or more light sources, one or more light detectors that generate the photoplethysmographic signal, a mounting element for attaching the photoplethysmographic system to a body part containing an artery having an actuator, a control system for controlling the actuator and the contact pressure of the photoplethysmographic system and an orthostatic level-correcting element, e.g. an accelerator, motion sensor or fluid-filled hose, placed next to the photoplethysmographic system used for heart level correction.

BRIEF DESCRIPTION OF THE FIGURES

An exemplary embodiment of the present invention is described herein with reference to the drawings, in which.

DETAILED DESCRIPTION

A wearable device and the accompanying method for the determination of continuous pulsatile BP are disclosed.

Absolute values can be obtained in the initial phase and how a transfer function can transform the BP-signal obtained at the finger or wrist to true BP-values corresponding to the brachial artery and at heart level. A one-time calibration method with NBP in order to determine the transfer function is disclosed.

The wearable device contains an orthostatic level-correcting element, for example an accelerator or motion sensor, which can measure the vertical distance between heart level and finger/wrist level, where the actual measurement takes places. The orthostatic pressure difference can be calculated and the BP-signal can be corrected to heart level pressure values, which is used for regular BP-measurement.

The wearable device has different operating modes. One mode is for the continuous measurement of hemodynamic parameters. In this mode, the contact pressure CP(t) is adaptively changed to mean arterial blood pressure (mBP) or a fraction of mBP.

Another mode is the initialization mode, where systolic, diastolic and mean arterial BP (sBP, dBP, mBP) is determined. Mean arterial BP (mBP) is the starting point for the continuous BP-measurement. sBP and dBP are used for the correct determination of the transfer function in order to correct the BP-signal obtained at the finger/wrist to central values. This is used for a correct clinical interpretation of BP. With this special initialization mode where actual sBP, dBP and mBP can be determined, the need for a calibration to NBP is eliminated or at least reduced to a one-time personalization of the transfer function to central BP-values before using the device.

A further mode may be an idle mode, where the contact pressure is reduced to 30-40 mmHg. The PPG-signal is still measured and can be used for heart rate detection. The system can be automatically switched into initialization and further to measurement mode by the motion sensor, when a fall of the patient is detected. Another trigger for switching into initialization and further measurement mode can be an unexpected increase or drop in heart rate or different timed intervals.

Further, the wearable device has elements for wirelessly transmitting signals to host devices like smart phone, tablet or other computers. The wearable device can be in the form of a ring or a watch or bracelet, for example.

Figure 1:
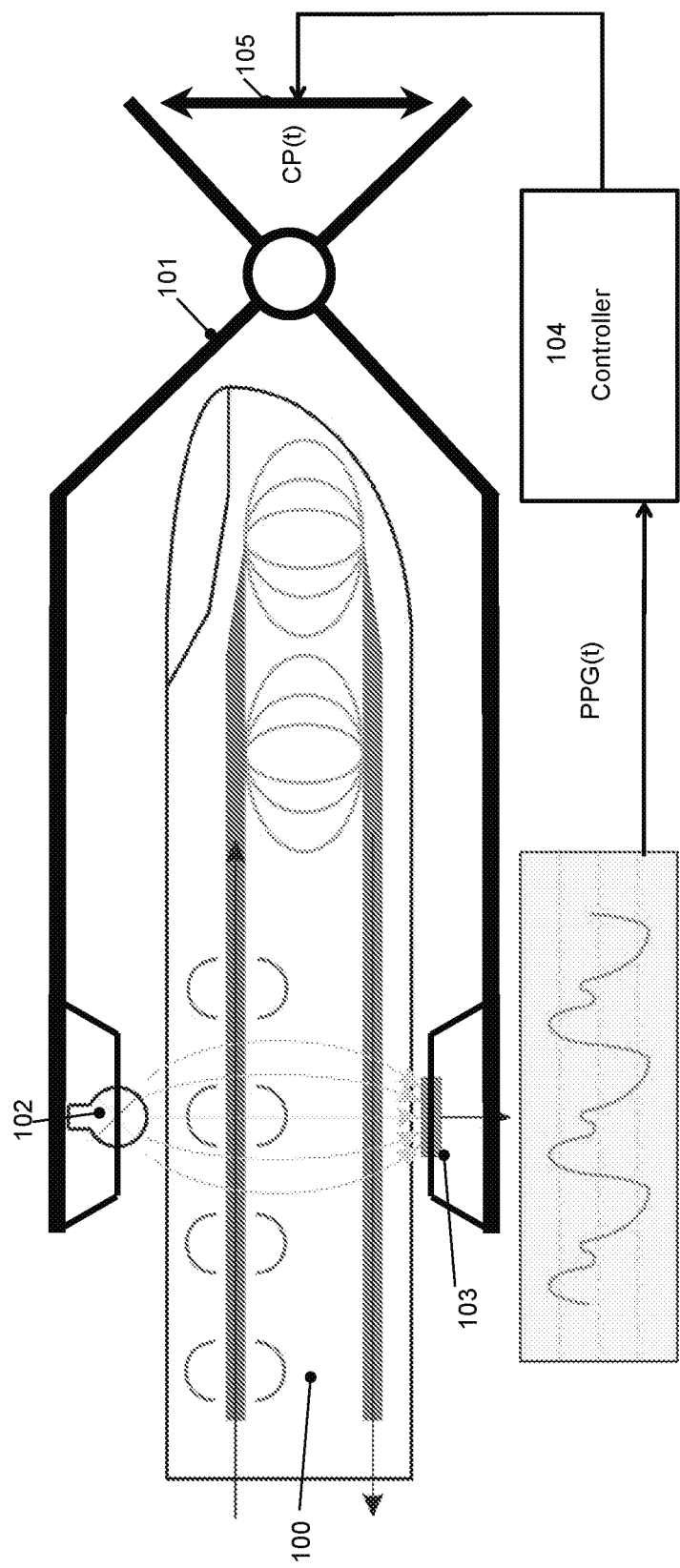
FIG. 1 shows the prior art method of measuring continuous, non-invasive pressure (BP) by means of a photoplethysmographic (PPG) system.

FIG. 1 shows a prior art system 101 placed on a finger 100. The system 101 includes one or more light sources 102, preferably LEDs, and one or more light receivers 103, which generates a photoplethysmographic (PPG) signal PPG(t). PPG(t) is the input for a controller 104. The controller 104 is altering the contact pressure CP(t) of the PPG-system using an actuator 105. The altering contact pressure CP(t) follows true mBP with the help of the controller 104.

Figure 2:
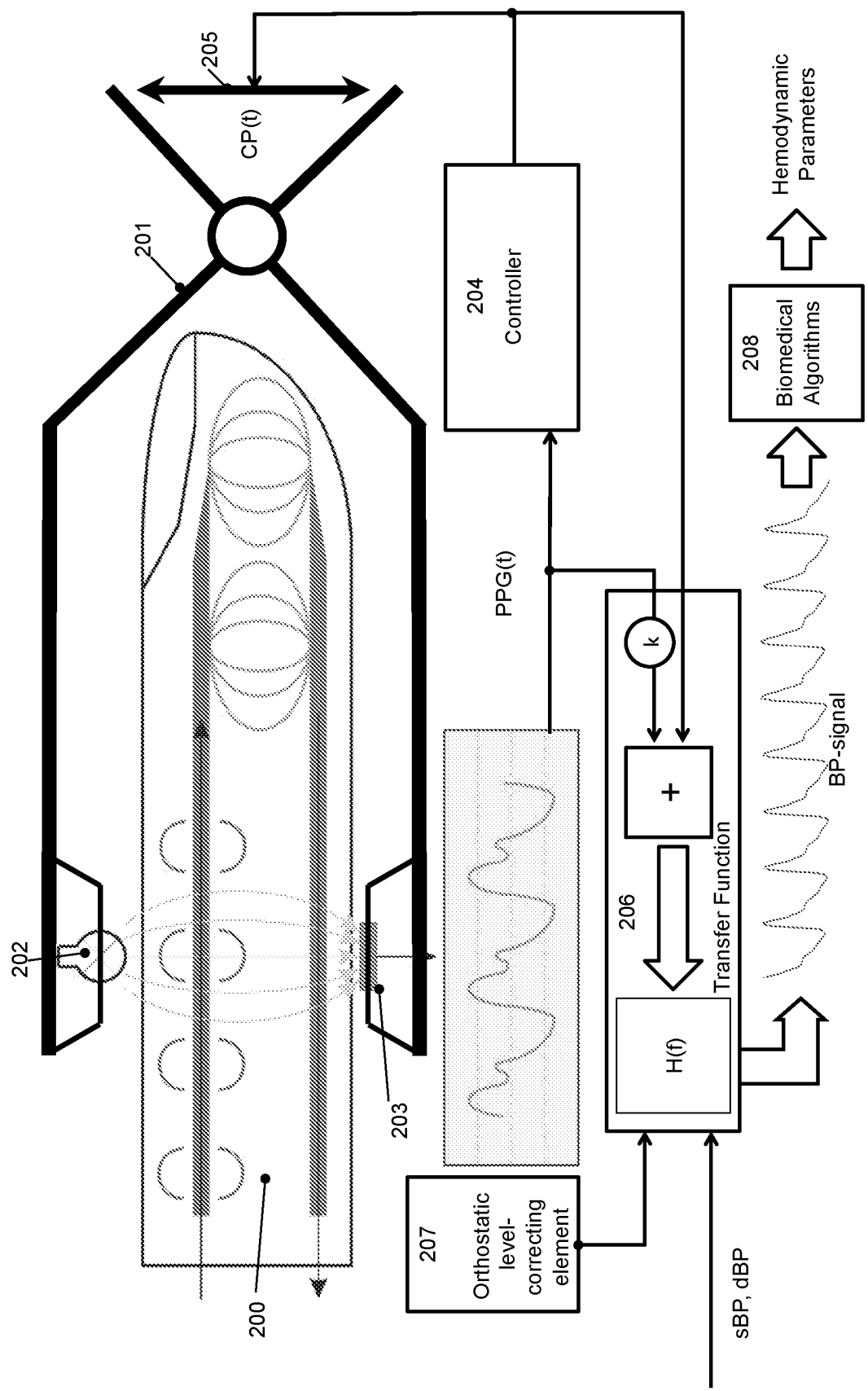
FIG. 2 shows a method of continuous non-invasive measurement of hemodynamic parameters within a wearable device of the present application.

FIG. 2 shows the system of the present application including the measurement of clinical relevant BP. Elements 200 to 205 are analogous to FIG. 1. In order to obtain clinical useful BP-values and a true continuous BP-signal, the finger BP is corrected to central values by using a mathematical transfer function 206. For that transfer function, PPG(t) is generated by the one or more light receivers 203, and CP(t) applied from the actuator 205 are used. Further, initial values of the transfer function 206, for example individual systolic and diastolic BP, may be obtained in an initial phase and/or during a one-time calibration to individual values of the patient before starting using the device. The transfer function 206 may be implemented in software that runs on a microcontroller or other computer.

For clinical use, BP must be measured at heart level or must be corrected to that level, if the location of the BP-sensor differs. In the daily use, the point of measurement of the sensor typically differs from heart level. In order to continuously correct the BP-signal obtained from the present sensor at the finger or wrist to heart level, an orthostatic level-correcting element 207 is used. This orthostatic level-correcting element 207 is in general measuring or calculating the pressure (orthostatic) difference between heart level and the point of measurement.

For this correction, the transfer function 206 receives information from the orthostatic level-correcting element 207, for example an accelerator or motion sensor, which can continuously measure the vertical distance between heart level and finger/wrist level, where the actual measurement takes places. The orthostatic BP difference can be calculated using the known blood density and the vertical distance. Thus, the BP-signal can be corrected to heart level pressure values, which is important for regular BP-measurement.

In a further embodiment, the orthostatic level-correcting element 207 could be a fluid-filled hose between the PPG-system and heart level is used as orthostatic level-correcting element (not shown). The hose is filled with a fluid having a density similar to that of blood. Otherwise a correction factor c must be used, where c is the fraction of the density of blood to the density of the fluid used. One end is closed with a freely floating membrane and the other end with a standard pressure sensor. The value obtained from this heart level pressure sensor multiplied with correction factor c equals to orthostatic BP difference and can be used for heart level correction.

Further hemodynamic parameters could be obtained from the pulsatile BP-signal using mathematical biomedical algorithms 208. One type of biomedical algorithms 208 could be a Pulse Contour Analysis method for the determination of cardiac output, stroke volume, peripheral resistance etc. Other parameters, especially parameters for the assessment of the autonomic nervous systems may be calculated by using further mathematical methods known from the art. The biomedical algorithms 208 may be implemented in software that runs on a microcontroller or other computer.

Preferably, the calculation of the BP-signal using the transfer function 206, the correction to heart level 207, as well further biomedical algorithms 208 takes place in one or more microcontrollers or computers (μCs) using software. These μCs can be placed either in the system 201 and/or on a smart phone, tablet or other computer connected to the Internet (see for further explanation FIG. 7).

Figure 3:
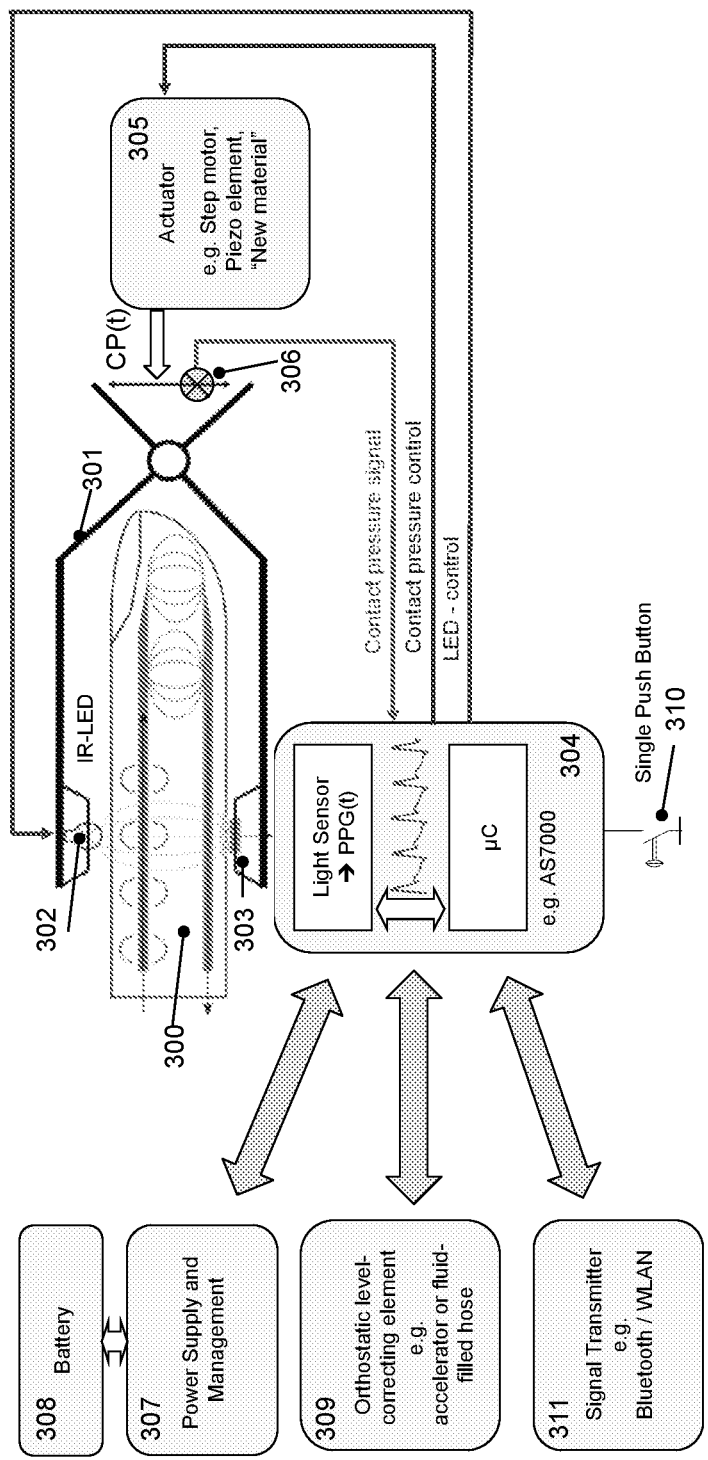
FIG. 3 shows the general block diagram and the hardware elements of the present application.

FIG. 3 shows the general block diagram and the hardware elements of the system. The system 301 is connected to a finger 300 and includes one or more light transmitters 302, preferably LED's with different wavelengths, and one or more light receivers 303 generating a PPG-signal PPG(t). The PPG-signal is sent to a controller unit 304 preferable a microcontroller or other type of computer using software. For example, the microchip AS7000 (ams AG, Unterpremstaetten, Austria) is a combined optical light receiver with a digital processor that may be used for measuring PPG(t) and further controlling the contact pressure CP(t) with an actuator 305.

In a basic embodiment, the microcontroller μC 304 controls contact pressure CP(t) using the actuator 305, measures the contact pressure CP(t) by using a pressure sensor 306, controls the one or more light transmitters LED's 302 and receives the PPG-signal PPG(t) from the one or more light receivers 303.

A pressure sensor 306 is used in combination with the actuator 305. The pressure sensor 306 will directly measure CP(t) and thus increase accuracy of the CP(t) measurement, which is a major input to the final BP-signal. In an alternative embodiment, the contact pressure CP(t) could be derived from the control signal of the actuator 305.

The actuator 305 could be a step motor, piezo element, or a "new material" that alters its dimension by applying an electrical signal to its surface. Ideally, no energy should be needed for "holding" the pressure. As mentioned above, the pressure sensor 306 is included for an accurate measurement of CP(t).

The μC 304 could further calculate the above mentioned mathematical transfer function 206 as well as the biomedical algorithms 208 like a pulse contour analysis for stroke volume and cardiac output measurement and further biomedical calculations e.g. for the assessment of the autonomic nervous system.

The μC 304 could be further connected with a power supply and power management unit 307, which receives and manages the power from a preferably loadable battery 308. The power received from the battery 308 can therefore optimized depending on the energy needs in different operation modes. This unit is also responsible for loading the battery 308.

For clinical use, BP must be measured at heart level and thus an orthostatic level-correcting element 309 is connected to the μC 304. In one embodiment, the orthostatic level-correcting element 309 could be the previously described fluid-filled hose.

In another embodiment, the orthostatic level-correcting element 309 could be an accelerator or motion sensor. For example, the microchips LIS3DH (STMicroelectronics) or the FXLS8471QFS (Xtrinsic) represent such accelerators or motion sensors which could be used for continuous calculating the vertical difference between heart and location of the sensor.

For zeroing the accelerator or motion sensor, a push button 310 is connected to the μC 304. During the zeroing procedure, the sensor is held at heart level and the button 310 is pushed to indicate zero orthostatic difference. Ideally, a short press or double press on the button indicates zeroing, as long presses may switch the sensor on and off. The μC 304 stores the actual vertical value of the accelerator or motion sensor 309 and can then continuously calculate the difference between the stored value and the new actual vertical value. Thus, the orthostatic pressure can be calculated from the vertical difference and the density of blood. In another embodiment, as BP is measured in Millimeters of Mercury (mmHg), the scaling factor between mmHg and centimeter water column (cmH$_2$O) can be used for the calculation of the orthostatic pressure, when the difference in cm is known. The resulting value must be corrected with the relative density of blood.

The accelerator or motion sensor 309 can detected heavy motion artifacts and disturbed signals could be marked. A further zeroing procedure will be needed, which could be indicated on the host device. A further indicator for re-zeroing could be an alternating swing of the contact pressure CP(t).

For the transmission of the BP-signal to a smart phone, tablet or another computer preferable connectable to the Internet, a signal transmitter 311 is connected to the μC 304. This transmitter could be WLAN or Bluetooth or any other available sender. This unit may also receive information from the host.

Figure 4:
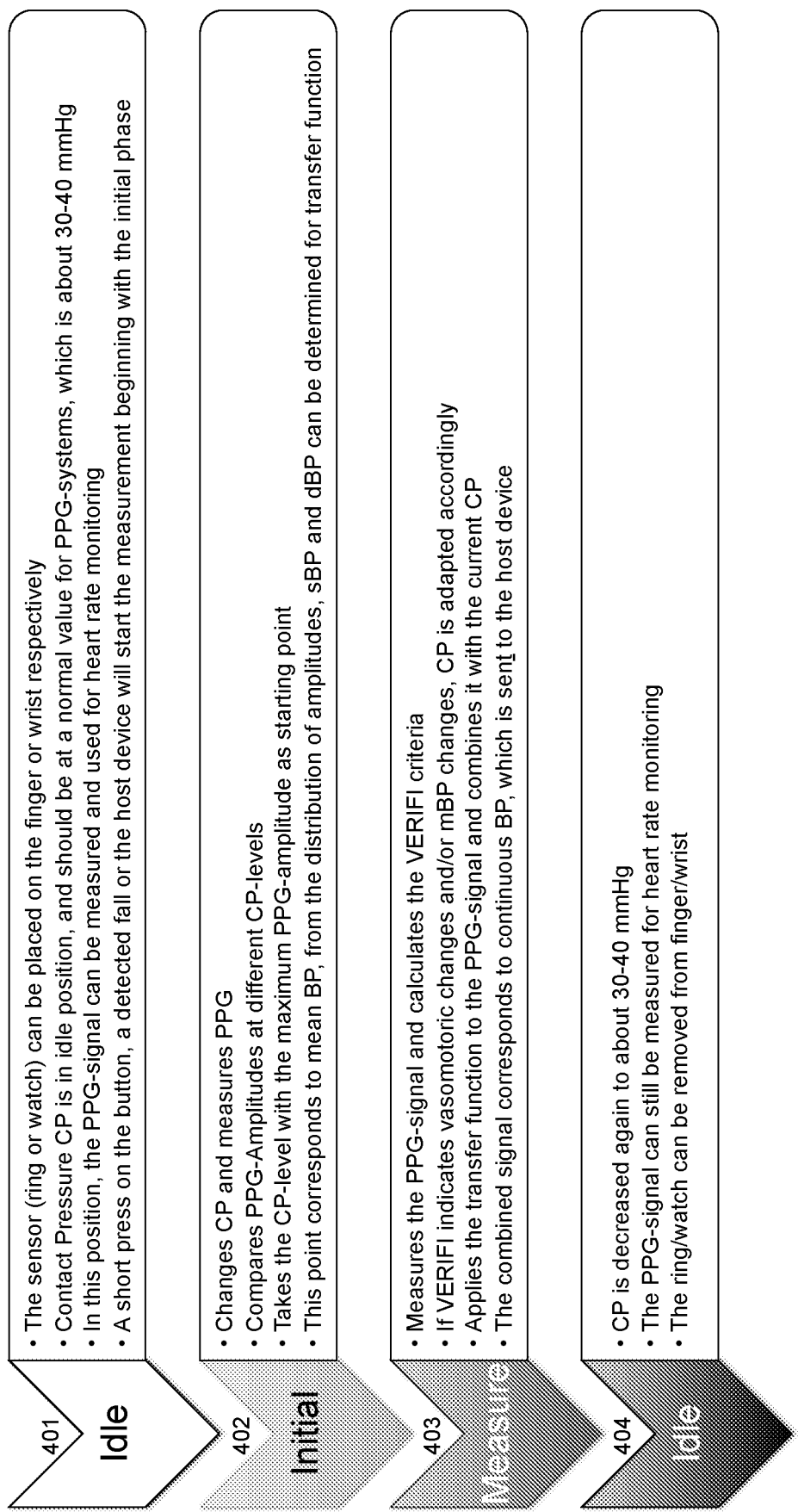
FIG. 4 is a flowchart showing the different operating modes of the system of the present application.

FIG. 4 is a flow chart showing the different operation modes of the system. After switching the sensor on, the device will be in idle mode 401. The sensor (ring, watch, or bracelet) can be placed on the finger or wrist respectively, as the contact pressure CP(t) is in idle position. It should be at a normal value for PPG-systems, which is about 30-40 mmHg. The system starts measuring the PPG-signal, which is now used for heart rate monitoring. A press on the button, a detected fall, immediately increase or decrease of heart rate or the host device will start the measurement beginning with the initial phase 402.

In the initial phase 402, CP(t) is adjusted by the control system and the actuator to different pressure levels. PPG(t) is measured, especially the PPG-amplitude is compared at different CP-levels. mBP can now be determined at the optimal contact pressure CP$_{OPT}$, where coevally the highest amplitude of the photoplethysmographic signal is measured. This mBP multiplied by a constant factor can now be used as the starting point CP$_{Start}$ for the measurement mode 403.

In addition to mBP, systolic and diastolic blood pressure sBP and dBP can be estimated using the distribution of the amplitude of PPG(t) versus the applied CP. Typically the distribution of the PPG-amplitudes is according to an envelop-curve, where the width of the envelope corresponds to Pulse Pressure (sBP minus dBP). sBP and dBP can be estimated according to this so-called oscillometric method.

In measurement mode 403, the PPG-signal is measured and the controller calculates the so-called VERIFI criteria (as described in WO 2013178475) for continuously altering CP(t) to mBP. If VERIFI indicates vasomotoric changes and/or mBP changes, CP(t) is adapted accordingly. The transfer function is applied to PPG(t) and to the current CP(t) in order to achieve the continuous BP. Either the resulting BP-signal is send to the host device and/or the underlying components PPG(t), CP(t) and the continuous vertical difference between heart level and sensor level. Biomedical algorithms are further calculating hemodynamic parameters from the true pulsatile BP-signal.

The device can be switched back to a further idle mode 404 by decreasing CP(t) again to about 30-40 mmHg. The PPG-signal can still be measured for heart rate monitoring or the ring/watch can be removed from finger/wrist. Power management can reduce energy for a longer battery life.

In this idle mode 404, the system works also as a surveillance monitor. The previously described accelerator or motion sensor may detect falls of the patient and switches first to the initialization mode 402 and afterwards to measurement mode 403. When the BP signal is submitted to a smart phone, an emergency may be called for a patient's safety. Zeroing the orthostatic level-correcting element will be not as important as it can be assumed that the patient lies on the floor and thus the sensor is likely on heart level.

Figure 5:
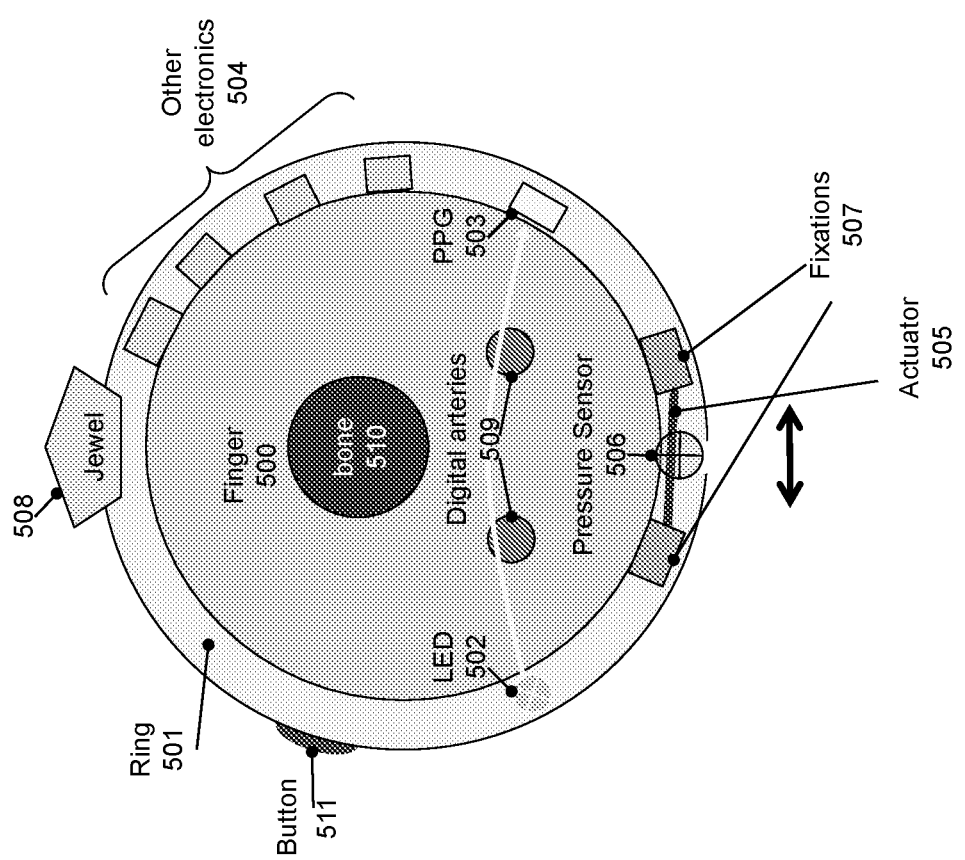
FIG. 5 shows an example embodiment of a wearable device of the present application.

FIG. 5 shows the sensor configured as a ring 501 worn on a finger 500, preferably on the index, middle or ring finger. The ring placed on the first phalanx is likely the most artifact free implementation. A ring can easily alter its CP by changing its circumference using, for example, actuators 505, such as a step motor in a "hose clamp" mechanic, a piezo element changing the circumference, or "new material" changes the circumference. This "new material" is able to change its dimensions by applying an electrical signal to its surface. The actuators 505 are placed on fixators 507. The contact pressure CP(t) is measured using a pressure sensor 506.

The other electronic 504 elements like μC, motion sensor, wireless transmitter, power manager, battery etc. shall be place inside the ring according to the FIG. 5. One push button 511 for start/stop and heart level adjustment should be added.

A "jewel" 508 may indicate correct placement for PPG-sensors especially the light sensors 502 and 503. As can be seen in FIG. 5, the finger 500 contains two digital arteries 509, which are palmar/volar sided to the finger bone 510. The best PPG-signal can be obtained, when the light sensors 502 and 503 are placed left and right to the finger according to FIG. 5 and the "jewel" 508 is therefore in the correct dorsal direction.

Figure 6:
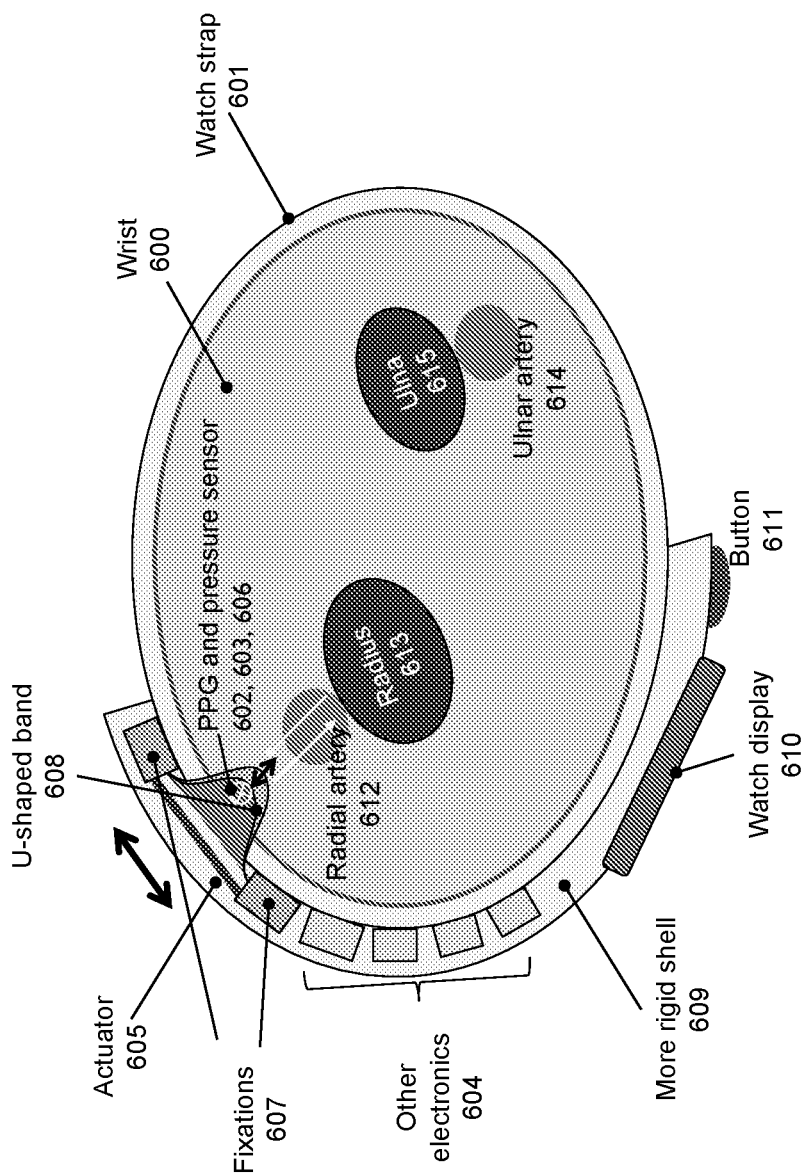
FIG. 6 shows another example embodiment of a wearable device of the present application.

FIG. 6 shows the sensor configured as a bracelet or watch 601 worn on the wrist 600. On a wrist, simply changing the diameter cannot alter CP(t) to the radial artery 612. Instead, a U-shaped band 608 connected to fixations 607 is part of the bracelet or watch 601. The bracelet or watch 601 should be placed in such a way that the U-shaped band 608 is at the location, where the radial artery pulse can be palpated. This radial pulse is generated in the radial artery 612 and amplified by the reflection at the radius 613. The system 601 can alter the depth of its 'U' with an actuator 605—when the actuator 605 constricts, the depth of the U-shaped band 608 increases and CP(t) increases too.

The pressure sensor 606 may be placed on the trough of the U-shaped band 608. Further, there must be space for the PPG-elements 602 and 603, which then receive the light signals reflected on the radius. The PPG signal will help with finding the correct placement of the sensor. The other electronic elements 604 like µC, motion sensor, wireless transmitter, power manager, battery etc. shall be place in the "more rigid shell" 609. With that configuration, a free blood flow in the ulna artery 614 beside the ulna 615 is guaranteed. The embodiment as a watch will further allow for user interaction on the watch display 610. A push button 611 for start/stop and heart level adjustment should be added.

Figure 7:
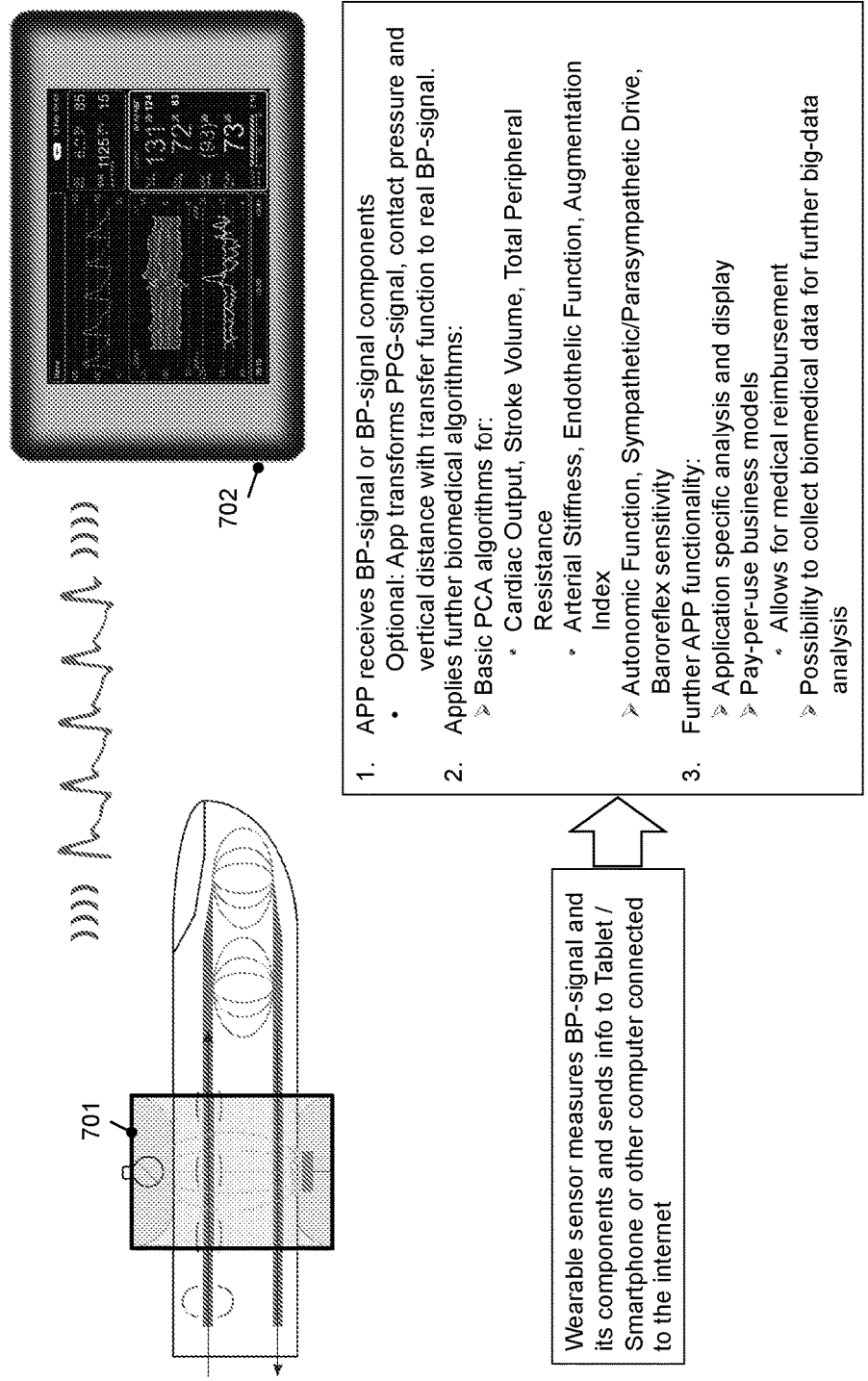
FIG. 7 shows the present application in use with another device.

FIG. 7 shows the transmission of the BP-signal and/or its components like PPG-signal, contact pressure, and vertical distance from the wearable device 701 to a smart phone, tablet or other computer 702 that may be connected to the Internet. An APP is further calculating hemodynamic and other parameters as well as software for displays, reimbursement models and other functionality. The functionality of the APP is shown in FIG. 7.

The APP performs the following functions:
  receives unfiltered BP-signal and its components from sensor;
  sends control information to the sensor;
  allows for software-update of the sensor;
  calculates further hemodynamic, autonomic and vascular parameters;
  has possibilities for displaying these further hemodynamic, autonomic and vascular parameters in a user-friendly and self-explanatory way;
  transmits and stores information;
  allows for different business models;
  supports reimbursement from health care system;

As mentioned above, the system further includes a transfer function 208. This transfer function includes different parts. The first part is the contact pressure CP(t), which adaptively changed to mBP or a constant factor $c_1$ multiplied with mBP (as described in to WO 2013178475). Thus, mBP in a distal part of the body typically at the finger or wrist is measured using CP(t) or $CP(t)/c_1$.

The next part is the pulsatile PPG(t) that can be used for the continuous BP-signal. The PPG(t) must be amplified by a gain factor k. The resulting finger BP-signal is:

$$BP_f(t) = CP(t)/c_1 + k*PPG(t)$$

where k can be estimated from the sBP and dBP values measured during initial mode. $PPG_{sys}$ and $PPG_{dia}$ are the corresponding PPG(t) values to sBP and dBP:

$$k = (sBP - dBP)/(PPG_{sys} - PPG_{dia})$$

The finger BP-signal must then be corrected to heart level by using the previously described vertical distance $d_v$ and the converting factor of [mmHg] to [cmH$_2$O], which is 0.73556 as well as to the relative density of blood $\rho_{Blood}$ which is 1.0506 (95% confidence interval: 1.0537–1.0475) at 37° C.

$$BP_f(t) = CP(t)/c_1 + k*PPG(t) + 0.73556*d_v*\rho_{Blood}$$

When the fluid-filled hose is used for heart level correction, the true orthostatic pressure difference $p_o(z)$ is measured.

$$BP_f(t) = CP(t)/c_1 + k*PPG(t) + p_o(z)$$

BP changes along the arterial pathway and peripheral $BP_f$ measurements need to be transferred to values that are comparable to standard values obtained at the brachial artery. This part of the transfer function 206 is typically a shift of frequency components H(f) and there are well known concepts out using a general transfer function.

This general transfer function H(f) of 206 may be personalized with a calibration performed before the first use. Upper arm cuff BP-values shall be obtained while the initial mode calculates finger sBP and dBP. These values, upper arm cuff sBP and dBP as well as finger sBP and dBP, can be used for a personalized general transfer function H(f) to get a proximal BP-signal.

The transfer function 206 in general as well as all parts of this transfer function 206 may be implemented in software that runs either on the microcontroller 304 or in the APP on the smart phone, tablet or other computer 702.

A further embodiment is the additional use as a pulse oximeter. Typically the system will work at the isosbestic point of oxyhemoglobin and desoxyhemoglobin at wavelength $\lambda_{CNAP}$=805 nm. When the LED's are exchanged by bi-color LED's working at pulsoxy wavelength ($\lambda_{red}$=660 nm, $\lambda_{IR}$=910 nm), the sensor can work as SpO$_2$ ring or watch too by using a state-of-the-art pulse oximeter method.

While a number of exemplary aspects and embodiments have been discussed above, those of skill in the art will recognize that still further modifications, permutations, additions and sub-combinations thereof of the features of the disclosed embodiments are still possible. It is therefore intended that the following appended claims and claims hereafter introduced are interpreted to include all such modifications, permutations, additions and sub-combinations as are within their true spirit and scope.

The invention claimed is:

1. A wearable device for measuring hemodynamic parameters comprising:
  a photoplethysmographic system having:
  one or more light sources;
  one or more light detectors that generate the photoplethysmographic signal;
  a mounting element for attaching the photoplethysmographic system to a body part containing an artery having an actuator;
  a control system for controlling the actuator and the contact pressure of the photoplethysmographic system; and
  an accelerator or motion sensor placed next to the photoplethysmographic system used for heart level correction;
  wherein the hemodynamic parameters are further derived from a transfer function;
  wherein the control system is configured to implement at least one of different modes of operations A to C:
  a mode A for continuous measurement of hemodynamic parameters, wherein the contact pressure is adjusted by the control system and the actuator according to mean arterial pressure multiplied by a constant factor; and wherein the transfer function is applied to the photoplethysmographic signal and the contact pressure;

a mode B for the initialization of the continuous measurement of hemodynamic parameters, wherein the contact pressure is adjusted by the control system and the actuator to different pressure levels;

wherein the amplitude of the photoplethysmographic signal is determined;

wherein mean blood pressure is determined at the contact pressure, where the highest amplitude of the photoplethysmographic signal is measured; and wherein the mean blood pressure multiplied by a constant factor is used as the starting point for the measurement modus; and an idle mode C, wherein the contact pressure is adjusted to a constant pressure around 30-40 mmHg; and wherein the system waits for user interaction in order to bring the system in initialization and further into the measuring mode;

wherein the photoplethysmographic signal is measured for obtaining heart rate; and wherein the system can be further brought in initialization and thereafter into the measuring mode if heart rate increases over or decreases under a predefined threshold.

2. The wearable device of claim 1 wherein the contact pressure is measured by a pressure sensor.

3. The wearable device of claim 1 further comprising a transmitter for sending the resulting hemodynamic parameters to a host device that is connected to the Internet.

4. The wearable device of claim 1 wherein at least two or more light sources or wavelengths are used;

wherein the least one light detector generates two or more photoplethysmographic signals corresponding to the at least two or more light sources or wavelengths; and further comprising means for calculating oxygen saturation by using the at least two different photoplethysmographic signals.

5. The wearable device of claim 1 wherein the elements of the device are placed into a ring, wherein the circumference of the ring can be altered by the actuator.

6. The wearable device of claim 1 wherein the elements of the device are placed in a bracelet or watch, wherein the actuator changes the contact pressure of the bracelet or watch at the wrist, where the radial artery can be palpated.

* * * * *